US00PP34596P2

(12) United States Plant Patent
Lyrene et al.

(10) Patent No.: US PP34,596 P2
(45) Date of Patent: Sep. 20, 2022

(54) BLUEBERRY PLANT NAMED 'FL11-137'

(50) Latin Name: ***Vaccinium corymbosum* L.**
Varietal Denomination: FL11-37

(71) Applicant: Florida Foundation Seed Producers, Inc., Marianna, FL (US)

(72) Inventors: Paul M. Lyrene, Micanopy, FL (US); James W. Olmstead, Aptos, CA (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 17/576,191

(22) Filed: Jan. 14, 2022

(51) Int. Cl.
*A01H 5/08* (2018.01)
*A01H 6/36* (2018.01)

(52) U.S. Cl.
USPC ..... Plt./157

(58) Field of Classification Search
USPC ..... Plt./157
CPC ... A01H 5/08; A01H 5/00; A01H 5/02; A01H 6/36; A01H 5/368
See application file for complete search history.

(56) References Cited

U.S. PATENT DOCUMENTS

PP12,165 P2 10/2001 Lyrene

OTHER PUBLICATIONS

U.S. Appl. No. 17/576,179, filed Jan. 14, 2022, Lyrene et al.

*Primary Examiner* — June Hwu
(74) *Attorney, Agent, or Firm* — Dentons US LLP

(57) ABSTRACT

'FL11-137' is a new and distinct southern highbush blueberry (*Vaccinium corymbosum* L.) variety distinguished at least by a low chilling requirement, vigorous, upright growth habit, high early yield, good field disease resistance, and large fruit that are sweet and exhibit medium size, dry picking scars.

6 Drawing Sheets

Latin name of the genus and species of the plant claimed: *Vaccinium corymbosum* L.

Variety denomination: 'FL11-137'.

BACKGROUND OF THE INVENTION

The invention relates to a new and distinct hybrid variety of southern highbush blueberry (*Vaccinium corymbosum* L.) plant named 'FL11-137'. 'FL11-137' originated as a seedling that was generated from a cross performed in Gainesville, Fla. during February of 2008 between 'FL05-61' (unpatented), as the female (seed) parent, and 'FL08-08' (unpatented), as the male (pollen). The seedling was planted in a high-density field nursery in May of 2009, and the first fruit were evaluated in April of 2010. After the second year of fruiting in the original field, 'FL11-137' was propagated by softwood stem cuttings during the spring of 2011. The number 11-137 was assigned at the time the clone was propagated by cuttings. The softwood stem cuttings were rooted in Gainesville, Fla. during summer 2011. 'FL11-137' was established in a pre-commercial field experiment with 15-plant test plot during winter of 2011 for a variety test in Windsor, Fla. Based on the growth, yield and bush appearance of this plot, 'FL11-137' was repropagated by softwood stem cuttings and tested for ornamental purposes in summer 2016 in Loxley, Ala. These plots have been observed during flowering and ripening each year since establishment in Waldo, Fla. and Loxley, Ala., and no mutations or off-type plants have been observed.

SUMMARY OF THE INVENTION

'FL11-137' differs from its parents and all other known southern highbush blueberry plants. The following are the most distinguishing characteristics of 'FL11-137' when grown under normal horticultural practices in Florida: (1) a very low chilling requirement, particularly for the flower buds; (2) a vigorous, bushy growth habit; (3) earlier ripening (from mid-late March through mid-May, when grown as a deciduous plant in north central Florida); and (4) large, firm, berries that exhibit medium, dry picking scars.

Blueberry variety 'Emerald' (U.S. Pat. No. 12,165) is planted throughout the southeastern United States. 'FL11-137' is believed to be most similar to 'Emerald'. Nonetheless, 'FL11-137' and 'Emerald' can be readily and unambiguously distinguished at least based upon growth habit, the time at which their fruit is produced, and the size of the leaves. Plants of 'FL11-137' display a more upright habit and are larger in size compared to 'Emerald'. Plants of 'FL11-137' produce their fruit significantly earlier than those of 'Emerald' when no growth regulator is used, the leaves of 'FL11-137' are significantly larger than those of 'Emerald', and the fruit cluster of 'FL11-137' are loose compared to the tight cluster of 'Emerald'. 'FL11-137' is not like 'Emerald' particularly because of its growth habit and leaves size.

BRIEF DESCRIPTION OF THE DRAWINGS

'FL11-137' is illustrated in the accompanying photographs of 9-year old specimens, which show the plant's flowers, fruit, leaves, and form. Colors shown are as true as can be reasonably reproduced by photographic procedures and may differ from those cited in the detailed description, which accurately describe the colors of 'FL11-137'.

DETAILED BOTANICAL DESCRIPTION

Figure 1:
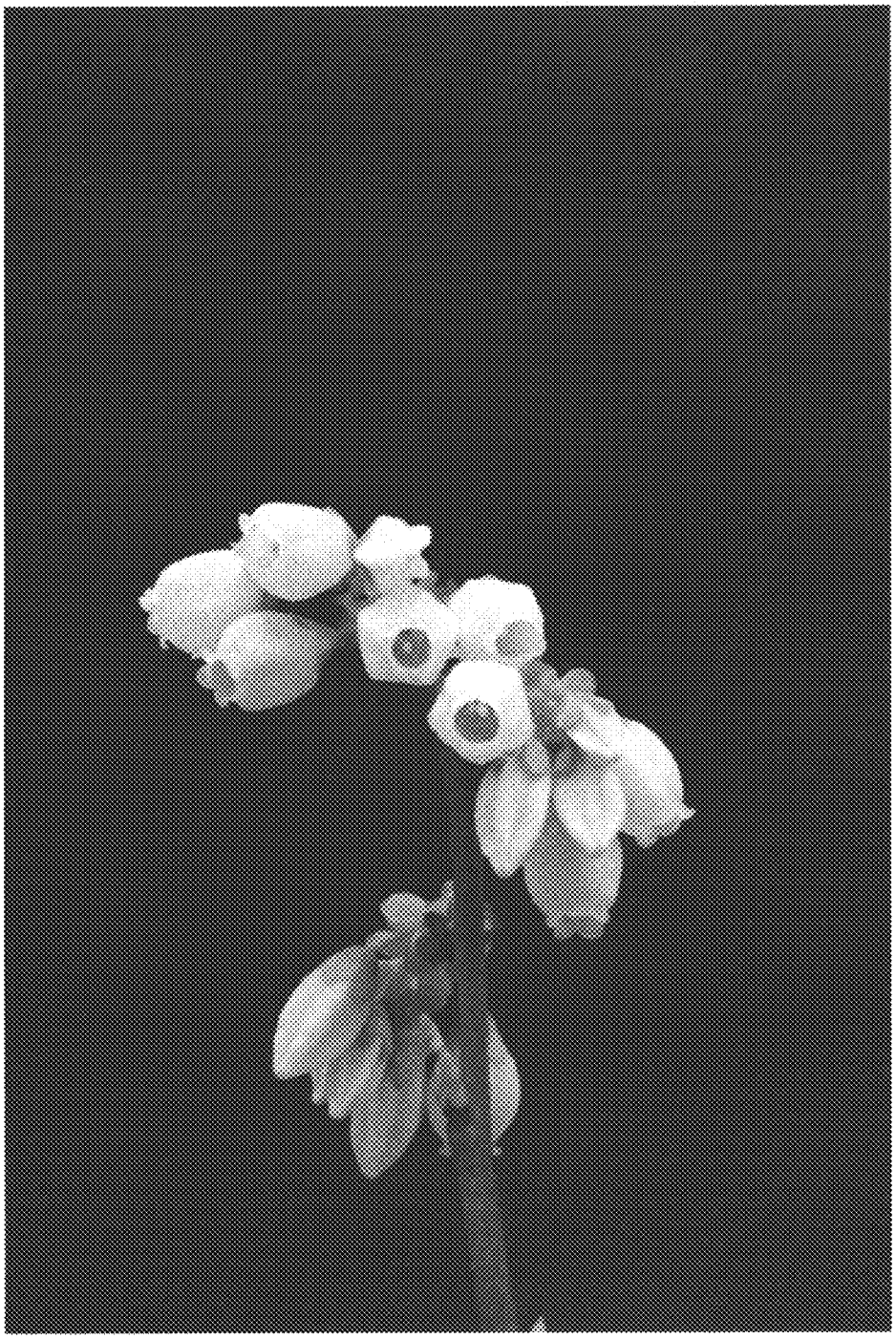
FIG. 1—Shows clusters of opening 'FL11-137' flowers on the branch.
Figure 2:
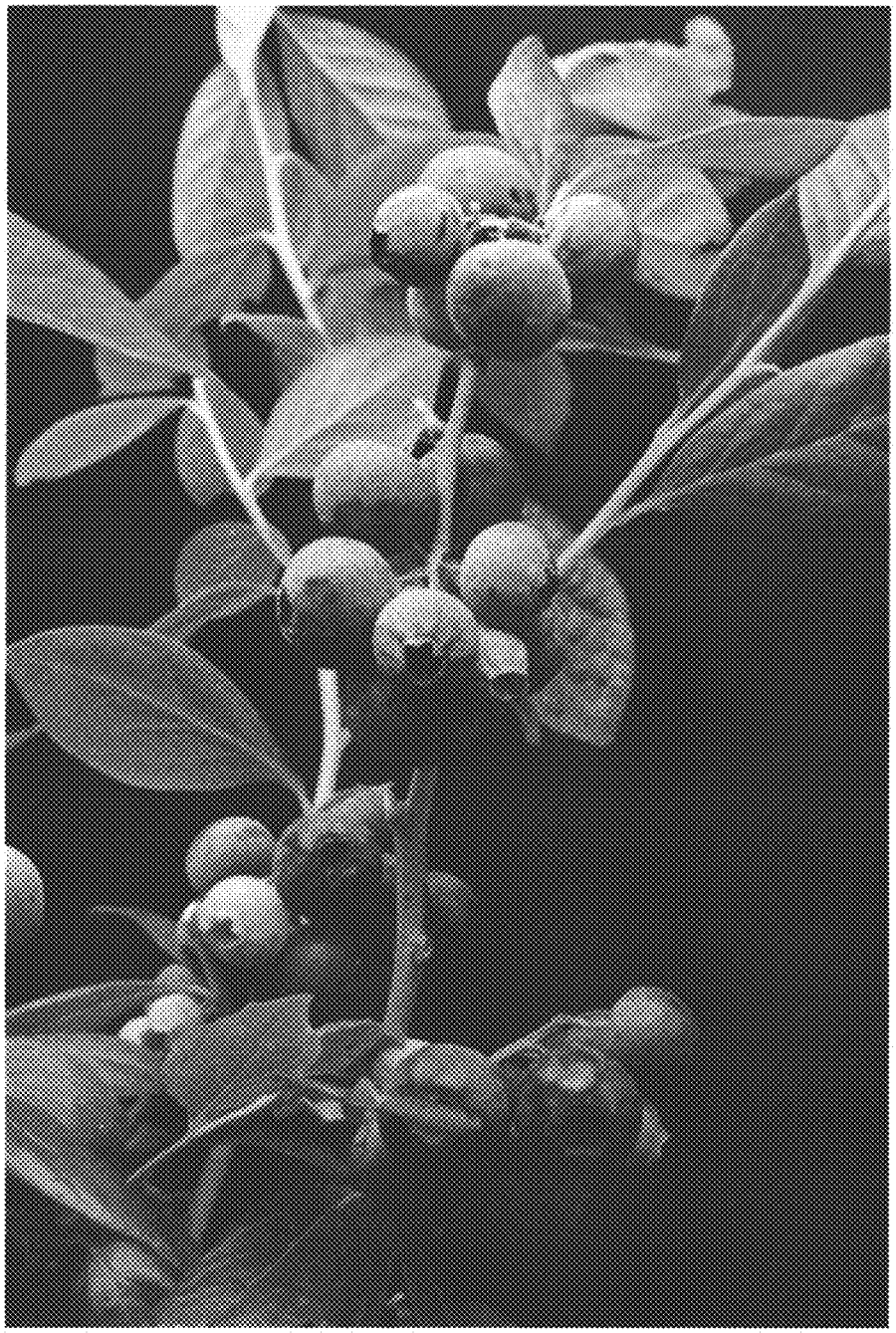
FIG. 2—Shows clusters of 'FL11-137' berry fruits on the branch.
Figure 3:
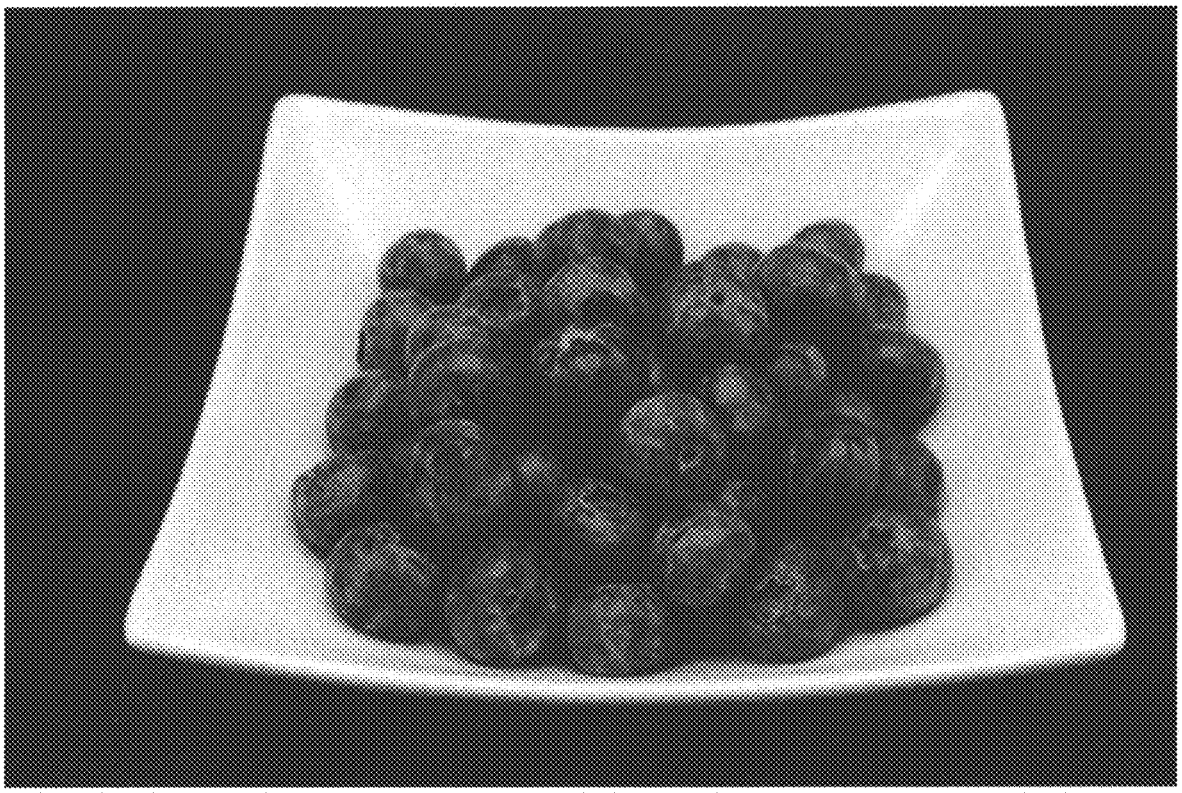
FIG. 3—Shows a close-up of harvested 'FL11-137' berries.
Figure 4:
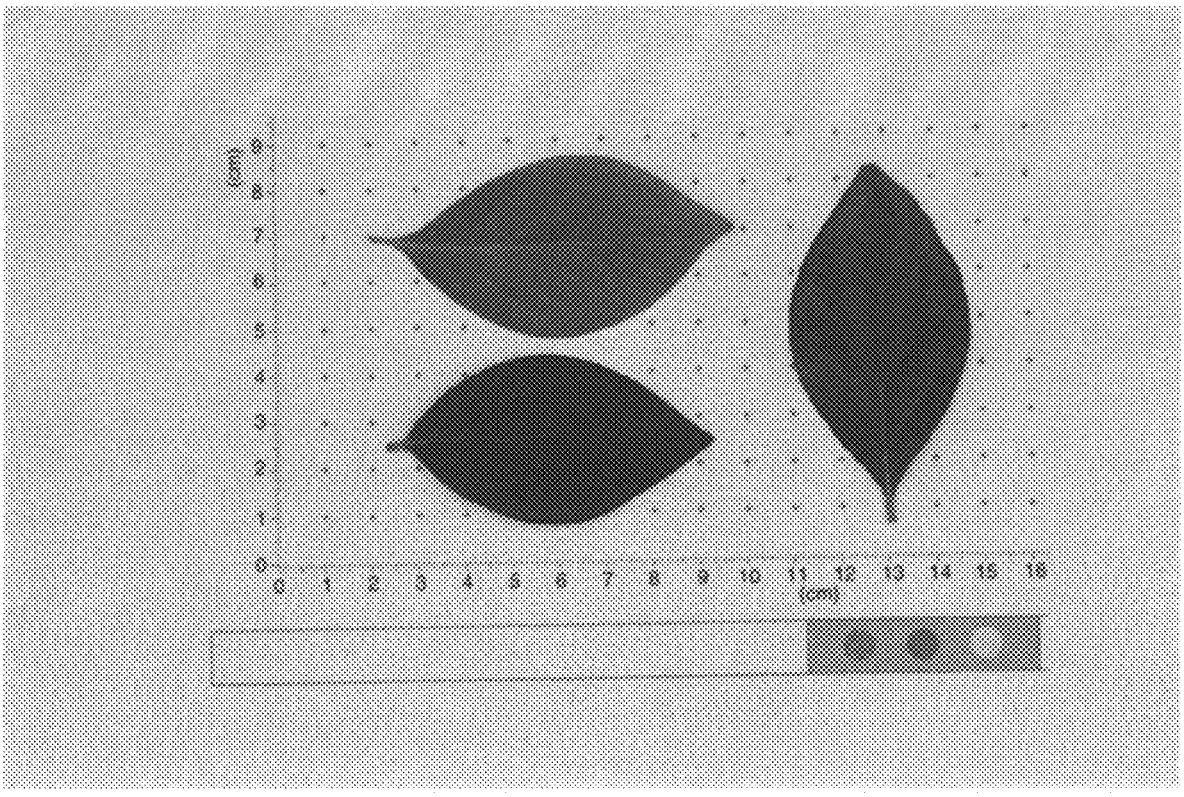
FIG. 4—Shows a close-up of mature 'FL11-137' leaves with a scale bar.
Figure 5:
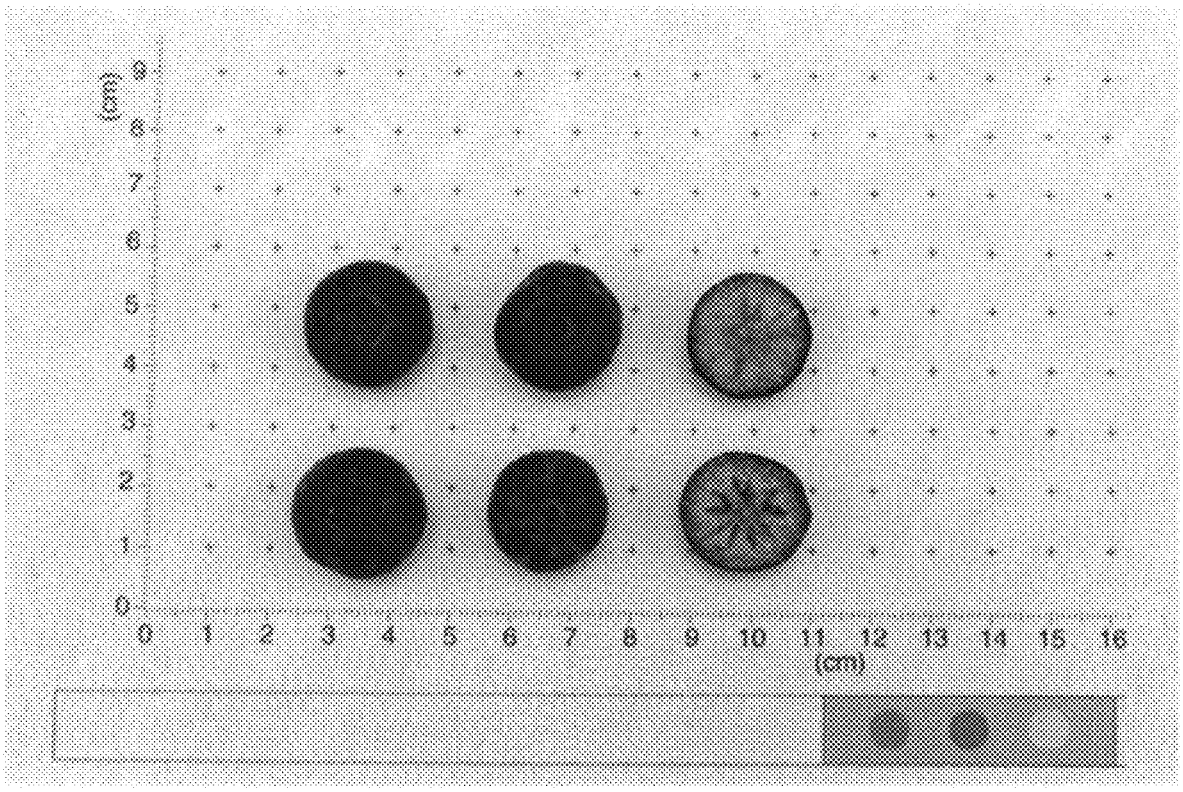
FIG. 5—Shows a close-up of mature 'FL11-137' fruit with a scale bar.
Figure 6:
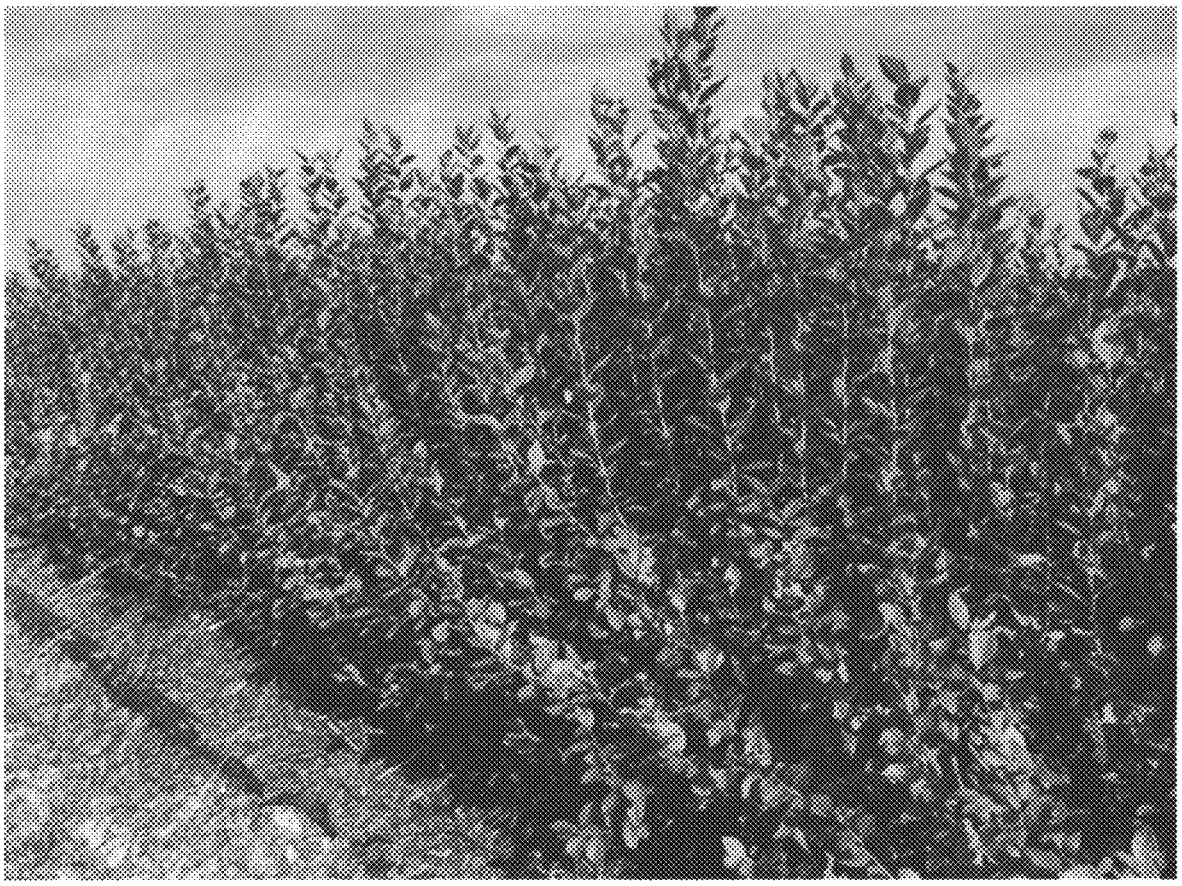
FIG. 6—Shows 7-year-old 'FL11-137' plants during the summer

The following detailed description sets forth distinctive characteristics of 'FL11-137'. The data that define these characteristics were collected from asexual reproductions carried out in Florida. The plant history was taken on a plot of plants growing in an experimental trial near Waldo, Fla. The plant was 8 years of age when the data was collected. Certain characteristics may vary with plant age. 'FL11-137' has not been observed under all possible environmental conditions, and the measurements given may vary when grown in different environments. Color descriptions are based on The Royal Horticultural Society (RHS) Colour Chart by The Royal Horticultural Society, London, Sixth Edition (2015). If any RHS color designations below differ from the accompanying photographs, the RHS color designations are accurate.

Classification:

*Family.*—Ericaceae.

*Botanical.*—*Vaccinium corymbosum* L.

*Common name.*—Southern Highbush Blueberry.

*Cultivar name.*—'FL11-137'.

Plant:

*Plant vigor.*—High.

*Growth habit.*—Upright Architecture.

*Plant height.*—1.82 m on average for 5-year old plant.

*Plant spread.*—1.75 m on average for 5-year old plant.

*Flower bud density (number) along flowering twigs in January.*—High.

*Twigginess.*—Low.

*Tendency toward evergreenness.*—Low, not an Evergreen candidate.

*Productivity.*—In northeast Florida, 'FL11-137' produces between 2 kg per season from plants 5 years old or older when hand harvested.

*Chilling requirement.*—150-200 hours below 7° C.

*Cold hardiness.*—'FL11-137' has been grown in temperate climates with extremely cold winter temperatures. Plants have survived winter freezes of −7° C. with minimal damage.

*Ease of propagation.*—'FL11-137' has only been propagated from softwood stem cuttings, where the rooting percentage is greater than 70% and comparable to other varieties.

Trunk and branches:

*Suckering tendency.*—Low.

*Surface texture (of strong, 12-month-old shoots observed in October).*—Moderately Smooth with a hint of presence of new developing bark-like structures.

*Surface texture (of 3-year-old and older wood).*—Moderately rough with presence of bark-like structures.

*Color of new twigs observed in the field.*—Fan 3 Yellow-Green Group 144 Strong Yellow Green B.

*Color of 3-year-old, rough-textured canes.*—Fan 4 Greyed-white Group 156 Yellowish Grey A with hints of Fan 4 Greyed-Orange Group 175 Dark Reddish Orange B.

*Internode length (strong, upright shoots measured in June).*—Mean of 16.96 mm.

Leaves:

*Leaf arrangement.*—Alternate, Fibonacci Spiral.

*Length (including petiole, from tip of petiole to end of blade).*—Mean of 8.14 cm.

*Width (at widest point).*—Mean of 4.66 cm.

*Petiole length.*—Mean of 5.12 mm.

*Petiole diameter.*—Mean of 1.76 mm.

*Leaf shape.*—Elliptic, with the leaf apex having a small-point extension(aristate).

*Leaf base shape.*—Elliptic, slight lanceolate.

*Leaf venation pattern.*—Reticulate.

*Margin.*—Entire.

*Color.*—Upper surface: Fan 3 Green Group 137 Moderate Olive Green A. Lower surface: Fan 3 Green Group 138 Moderate Yellow Green B. Leaf Vein Color: Fan 3 Yellow-Green Group N144 Strong Yellow B. Leaf petiole color: Fan 3 Yellow Green group 145 Light Yellow Green B.

*Pubescence.*—Upper surface of leaves: Absent. Lower surface of leaves: Absent. Margins: Absent.

*Timing of vegetative bud burst (early, medium, late).*—Medium.

*Relative time of leafing versus flowering.*—When not treated with hydrogen cyanamide in mid-winter, leafing occurs after flowering.

Flowers:

*Arrangement.*—Flowers are arranged Alternately on a short branch without leaves.

*Fragrance.*—No floral fragrance.

*Shape.*—Urceolate and cylindrical.

*Flowering period.*—Mean date of 70% anthesis at Waldo, Fla. is February 10.

*Cluster.*—Medium cluster density.

*Number of flowers per cluster.*—Mean of 6.

*Pedicel.*—Length at time of anthesis: Mean of 5.79mm. Color at time of anthesis: Fan 2 Red Purple Group 64 moderate Purplish Red A on the sun exposed side.

*Peduncle.*—Length at time of anthesis: Highly, variable, mean of 12.1 mm. Color at time of anthesis: Fan 2 Red-Purple Group 67 Strong purplish Red A on sun exposed side.

*Calyx.*—Surface texture: Smooth. Diameter: Mean of 6.04 mm. Color (outer surface, visible at the time of anthesis without removing the corolla tube): Fan 3 green group 138 moderate Yellowish Green A to Fan 3 green group 138 moderate yellow Green B on tips of calyx lobes.

*Corolla.*—Diameter: mean of 7.04 mm. Length (from pedicel attachment point to corolla tip excluding the pedicel): Mean of 11.55 mm. Aperture diameter: Mean of 2.48 mm. Texture: Smooth with slight radiations. Corolla Color: Fan 4 White Group 155 Greenish White C. Anthocyanin coloration in tube: Slight Presence.

Reproductive organs:

*Style.*—Length (top of ovary to stigma tip): Mean of 7.63 mm. Color: Fan 3 Yellow-Green Group 145 Strong Yellow Green A.

*Location of tip of stigma relative to lip of the corolla.*—Stigma tip is approximately even to 2.28 mm below the corolla lip.

*Anthers.*—Color: Fan 4 Greyed-Orange Group N167 Brownish Orange A. Pollen: High. Pollen germination: typically, greater 90%. Color: Fan 1 Yellow Group 8 Pale Yellow D. Filament length: 6.97 mm. Filament width: 1.21 mm.

*Self-fruitfulness.*—Low to medium. Planting in the field configurations that promote cross fertilization with other southern highbush varieties is recommended for all southern highbush blueberry plants grown in Florida.

Fruit:

*Mean date of 50% harvest in Waldo, Fla.*—Weeks 17-18.

*Diameter of calyx aperture on mature berry.*—Mean of 7.1 mm.

*Size and shape of calyx lobes on mature berry.*—Very small, erect to incurving, with a less than shallow calyx basin.

*Pedicel length on ripe berry.*—Mean of 8.03 mm.

*Detachment force for ripe berries* (*easy, medium, hard*).—Medium.

*Fruit cluster density* (*sparse, medium, dense*).—Medium.

*Number of berries per cluster.*—5.

*Fruiting type.*—On one-year-old shoots and none on current season's shoots.

Berry:

*Cluster* (*tight, medium, loose*).—Medium.

*Weight* (*on well-pruned plants*).—Mean of 1.9 grams per berry.

*Height.*—Mean of 14.9 mm.

*Width.*—Mean of 19.4 mm.

*Shape.*—Oblate, slightly convex on pedicel side and calyx side.

*Surface color of mature berries ripe on the plant.*—Fan 2 Violet-Blue Group 98 Light Blue C.

*Intensity of fruit bloom.*—Medium.

*Surface color of ripe berry after polishing.*—Fan 4 Black Group 203 Bluish Black C.

*Immature berry color, with bloom.*—Fan 3 Yellow-Green Group 145 Strong Yellow Green A.

*Immature berry color, without bloom.*—Fan 3 Yellow-Green Group 144 Strong Yellow Green B.

*Flesh color.*—Fan 3 Yellow-Green Group 147 Moderate Yellow Green C.

*Surface wax.*—Moderate and medium persistence.

*Pedicel scar.*—Medium and dry. Mean of 2.61 mm.

*Firmness.*—Firm.

*Flavor.*—Slightly sweet.

*Intensity of fruit sweetness.*—Low.

*Texture.*—Good texture, juicy with non-mealy flesh texture.

*Fruit storage quality.*—Fruit is unusually firm and can be stored without shriveling, mold or loss of firmness for 3 weeks at 4° C.

Seeds:

*Average weight of well-developed dried seeds.*—0.53 mg per seed.

*Length of well-developed dried seeds.*—Mean of 1.8mm.

*Width of well-developed dried seeds.*—Mean of 0.8 mm.

Use: Produces southern highbush blueberries suitable for hand harvest for backyard production.

Resistance to diseases, insects, and mites: 'FL11-137' has grown vigorously and shows good bush survival in the field, with none to very low number of plants dying soon after planting. Reaction to the various fungal species that cause summer leaf spots (including rust) is lower than those of other southern highbush varieties. Fungicide applications may be needed after harvest to reduce foliar and stem diseases and retain leaves into the fall for maximum flower bud set. Appears to be more tolerant than other southern highbush varieties to spider mites. Susceptibility to typical blueberry insect and mite pathogens such as spotted wing drosophila (*Drosophila suzukii*), blueberry gall midge (*Dasineura oxycoccana*), blueberry flower thrips (*Frankliniella* spp), and blueberry bud mite (*Acalitus vaccini*) appear similar to other southern highbush.

What is claimed is:

1. A new and distinct variety of southern highbush blueberry plant named 'FL11-137', as illustrated and described herein.

* * * * *